United States Patent
Malhotra et al.

(10) Patent No.: US 10,391,080 B2
(45) Date of Patent: Aug. 27, 2019

(54) KETOROLAC FOR THE TREATMENT OF CANCER

(71) Applicant: Cipla Limited, Mumbai (IN)

(72) Inventors: Geena Malhotra, Mumbai (IN); Kalpana Joshi, Maharashtra (IN); Jeevan Ghosalkar, Thane (IN)

(73) Assignee: Cipla Limited, Mumbai (IN)

( * ) Notice: Subject to any disclaimer, the term of this patent is extended or adjusted under 35 U.S.C. 154(b) by 0 days.

(21) Appl. No.: 15/645,544

(22) Filed: Jul. 10, 2017

(65) Prior Publication Data

US 2018/0021305 A1     Jan. 25, 2018

(30) Foreign Application Priority Data

Jul. 21, 2016 (IN) .............................. 201621025013

(51) Int. Cl.
    *A61K 31/407*     (2006.01)
    *A61K 45/06*     (2006.01)
    *A61K 31/404*     (2006.01)

(52) U.S. Cl.
    CPC .......... *A61K 31/407* (2013.01); *A61K 31/404* (2013.01); *A61K 45/06* (2013.01)

(58) Field of Classification Search
    CPC .................................................. A61K 31/407
    See application file for complete search history.

(56) References Cited

U.S. PATENT DOCUMENTS

2004/0127470 A1 *   7/2004   Masferrer .............. A61K 31/00
                                                                     514/165

OTHER PUBLICATIONS

Motzer et al., Overall Survival and Updated Results for Sunitinib Compared With Interferon Alfa in Patients With Metastatic Renal Cell Carcinoma, J Clin Oncol. Aug. 1, 2009; 27(22): 3584-3590.*
Cho et al., Prospective evaluation of analgesic use and risk of renal cell cancer, Arch Intern Med. Sep. 12, 2011;171(16):1487-93.*
Chow et al., Use of analgesics and risk of renal cell cancer. Int J Cancer. Nov. 15, 1994;59(4):467-470.*
Gago-Dominquez et al., Regular use of analgesics is a risk factor for renal cell carcinoma, Br J Cancer. Oct. 1999;81(3):542-8.*
Kaye at al., Acetaminophen and the risk of renal and bladder cancer in the general practice research database, Epidemiology. Nov. 2001;12(6):690-4 (Abstract).*
Sorensen et al., Risk of cancer in a large cohort of nonaspirin NSAID users: a population-based study, Br J Cancer. Jun. 2, 2003;88( 11):1687-92.*
Choueiri et al., Analgesic use and the risk of kidney cancer: a meta-analysis of epidemiologic studies, Int J Cancer, vol. 134(2), pp. 384-396, Jan. 15, 2014.
Hamieh et al., Impact of Aspirin and Non-Aspirin Nonsterdoidal Anti-Inflammatory Drugs on Outcomes in Patients with Metastatic Renal Cell Carcinoma, Kidney Cancer, vol. 2, pp. 37-46, 2018.

* cited by examiner

*Primary Examiner* — Svetlana M Ivanova

(74) *Attorney, Agent, or Firm* — Meunier Carlin & Curfman LLC

(57) ABSTRACT

Methods of treating cancer, including PAR-4 implicated cancers or renal cell carcinoma, using ketorolac are disclosed herein. Ketorolac can be administered as a monotherapy or as part of a comprehensive treatment program, which can also include administration with other anti-cancer drugs, surgical treatments or exposure to ionizing radiation.

15 Claims, 5 Drawing Sheets

KETOROLAC FOR THE TREATMENT OF CANCER

CROSS REFERENCE TO RELATED APPLICATION

This application claims the benefit of Indian Application 201621025013, filed on Jul. 21, 2016, the contents of which are hereby incorporated in its entirety.

FIELD OF THE INVENTION

The invention is directed to the treatment of cancer, especially PAR-4 susceptible cancers and/or renal cell carcinoma, using ketorolac, optionally in combination with one or more additional cancer therapies.

BACKGROUND

Cancer is a major public health problem in the United States and many other parts of the world. It is currently the second leading cause of death in the United States, and is expected to surpass heart diseases as the leading cause of death in the next few years. It remains a major cause of mortality in the world. Despite the improvements that have been made in therapies and in understanding the molecular basis of cancer, mortality is still high. The current treatment regimens for cancer have shown limited survival benefits when used for most advanced stage cancers.

The research and efforts being invested for cancer treatment has changed over the past few decades. The age when surgery and radiotherapy were the only effective ways to fight tumor growth has ended. A complex scenario where the molecular features of tumors seem to be the cornerstone of any therapy is now emerging with new targets or receptors being discovered in vivo. Continued research has expanded knowledge of how cancer develops and how to target medicines for specific cancer types, which has resulted in more effective therapies for patients. However these therapies show a lack of efficacy in terms of long-term outcome because of their failure to target cancer cells and lead to toxicity due to non-specific effects on normal cells. To overcome these side effects, researchers have tried to understand the root cause and have explored more about the gene changes in cells that cause cancer, they have been able to develop drugs that target these changes. Targeted therapy drugs does not work in the same way as the standard chemotherapy drugs. They are often able to attack cancer cells while doing less damage to normal cells by targeting the programming of cancer cells that sets them apart from normal, healthy cells. These drugs tend to have different (and often less severe) side effects than standard chemotherapy drugs. Examples of the targeted therapies include sorafenib, sunitinib, bevacizumab, telomerase etc.

Research on apoptosis has increased substantially since the early 1990s. Apoptosis (programmed cell death)-inducing drugs change proteins within the cancer cells and cause the cells to die.

Apoptosis can be initiated through one of two pathways. In the intrinsic pathway the cell kills itself because it senses cell stress, while in the extrinsic pathway the cell kills itself because of signals from other cells. Both pathways induce cell death by activating caspases, which are proteases, or enzymes that degrade proteins. The two pathways both activate initiator caspases, which then activate executioner caspases, which then cause cell apoptosis by degrading proteins indiscriminately.

Induction of apoptosis in malignant cells therefore becomes a major goal of cancer therapy in general and of certain cancer gene therapy strategies in particular. Numerous apoptosis-regulating genes have been evaluated for this purpose for example p53 gene, p16, p21, p27, E2F genes, FHIT, PTEN, E1A and CASPASE genes.

The prostate apoptosis response-4 (PAR-4) gene was first identified by the differential hybridization technique as an immediate early apoptotic gene upregulated in response to elevated intracellular Ca2+ concentration [Ca2+] in the androgen-independent rat prostate cancer cells AT-3 treated with ionomycin.

Studies conducted in cell culture models show that overexpression of PAR-4 is sufficient to directly induce apoptosis in many cancer cell types. The ability of PAR-4 to directly cause apoptosis is associated with its nuclear translocation. Moreover, the apoptotic action of PAR-4 can overcome cell protective mechanisms, such as the presence of Bcl-xL, Bcl-2, or absence of wild-type p53 or PTEN function. Interestingly, PAR-4 is incapable of directly inducing apoptosis in normal or immortalized normal cells.

The "apoptosis-sensitizing" function of PAR-4 in some of the cancer cells is attributed to its accumulation in the cytoplasm and inability to translocate into the nucleus, due to phosphorylation by Akt1 which renders PAR-4 subject to sequestration in the cytoplasm by complexing it with chaperone proteins such as 14-3-3; however, treatment with the other apoptotic signals translocates PAR-4 into the nucleus to produce apoptosis. Renal cell carcinoma (RCC, also known as hypernephroma) is a kidney cancer that originates in the lining of the proximal convoluted tubule, the very small tubes in the kidney that transport GF (glomerular filtrate) from the glomerulus to the descending limb of the nephron. RCC is the most common type of kidney cancer in adults, responsible for approximately 80% of cases. It is also known to be the most lethal of all the genitourinary tumors. Initial treatment is most commonly a radical or partial nephrectomy and remains the mainstay of curative treatment. Where the tumor is confined to the renal parenchyma, the five year survival rate is 60-70%, but this is lowered considerably once metastases have spread. It is relatively resistant to radiation therapy and chemotherapy, although some cases respond to immunotherapy.

Renal-cell carcinoma affects approximately 150,000 people worldwide each year, causing close to 78,000 deaths annually, and its incidence seems to be increasing. RCC is not a single entity, but rather comprises the class of tumors of renal epithelial origin. Extensive histological and molecular evaluation has resulted in the development of a consensus classification of different RCC subtypes: (i) conventional (clear-cell) renal cell carcinoma; (ii) papillary renal cell-carcinoma; (iii) chromophobe renal carcinoma; (iv) oncocytoma; (v) collecting-duct carcinoma. Although most cases of RCC seem to occur sporadically, an inherited predisposition to renal cancer accounts for 1-4% of cases and could involve the same genes that cause sporadic renal cancer. Over the past two decades, studies of families with inherited RCC have laid the groundwork for the identification of seven hereditary renal cancer syndromes, and the predisposing genes for five of these have been identified. The surprisingly diverse nature of these genes implicates various mechanisms and biological pathways in RCC tumorigenesis.

RCC can be treated using surgery, radiation therapy, immunotherapy, and molecular-targeted therapy. Surgical resection remains the only known effective treatment for localized renal cell carcinoma, and it is also used for palliation in metastatic disease. Targeted therapy and immunomodulatory agents are considered standard of care in patients with metastatic disease.

Options for chemotherapy and endocrine-based approaches are limited, and no hormonal or chemotherapeutic regimen is accepted as a standard of care. Objective response rates with chemotherapy, either single-agent or combination, are usually lower than 15%. Therefore, various therapies have been evaluated.

The first agent, approved in late 2005, was sorafenib, after showing improvement in the second-line setting for progression-free survival (PFS) versus placebo. Shortly thereafter, sunitinib was approved following a large phase III trial that also demonstrated improvement in PFS versus interferon-α (INFα) in the first-line setting. The next agent approved was the mechanistic target of rapamycin (serine/threonine kinase) (mTOR) inhibitor, temsirolimus, which was evaluated as a first-line therapy against INFα in patients, most of whom had poor-risk disease. This trial demonstrated an improvement in overall survival (OS) in patients receiving temsirolimus. Combination of temsirolimus and INFα showed no advantages over the mTOR inhibitor alone. Meanwhile, everolimus was the second mTOR inhibitor approved after second-line therapy showed improvement in PFS versus placebo in a clinical trial. Pazopanib and axitinib are the two newer tyrosine kinase inhibitors and were recently approved for treatment of metastatic RCC. Patients taking pazopanib exhibited improved PFS versus those taking placebo both in the first-line setting and for cytokine-refractory disease. Axitinib was studied against sorafenib as a second-line agent and demonstrated improved PFS, while patient preference studies with pazopanib suggested improved tolerability. Yet another class of drug, an anti-PD-1 checkpoint inhibitor named nivolumab, has been approved for intravenous administration that unleashes the body's immune system to fight the cancer cancer, however, the drug may cause the body to develop an immune reaction against its own tissues thereby leading to wide range of side effects that can be severe or life-threatening. With multiple approved agents available, further research is yet to define the ideal timing, sequencing, and patient profile for a given particular agent.

Although, studies have demonstrated the general tolerability of targeted agents, in most instances, patients with RCC typically develop resistance to targeted agents after a median of 5-11 months of treatment. Combinations of targeted agents are being evaluated, but toxicity is problematic. Several strategies have been tested to manage the drug resistance including: Adjusting the dose of the drug, combination therapy or switching to an alternative agent. Moreover alternative pathways are currently under investigation particularly targeting of RAF (Rapidly Accelerated Fibrosarcoma), MEK (Mitogen-activated protein/extracellular signal-regulated kinase), and the PI3K (Phosphatidylinositol 3-kinase)/AKT (a serine/threonine kinase also known as protein kinase B [PKB]) pathway.

Based on the information available, even though there have been some advancements in the treatment of renal cell carcinomas, the associated complications like the disease stage, the response rate and the accompanying side effects potentially reduce the patient compliance and poses issues which severely affect the progression-free survival (PFS) and/or the overall survival (OS) which is the ultimate treatment goal for a given therapy.

Thus there is a need for improved methods for treating cancer. There remains a need for selective PAR-4 agonists. There remains a need for identifying selective PAR-4 agonists useful in the treatment of cancer. There remains a need for improved and additional methods of treating renal cell carcinoma. There remains a need for additional small-molecule therapeutics for the treatment of renal cancer.

SUMMARY

According to an aspect of the present invention, there is provided a method for enhancing or promoting PAR-4 expression by administering a PAR-4 agonist. In some instances the PAR-4 agonist is non-steroidal anti-inflammatory drug, for instance ketorolac, or a pharmaceutically salt or ester thereof.

According to an aspect of the present invention, there is provided a method of treating cancer comprising administering by administering a PAR-4 agonist. In some instances the PAR-4 agonist is non-steroidal anti-inflammatory drug, for instance ketorolac, or a pharmaceutically acceptable salt or ester thereof.

According to an aspect of the present invention, there is provided a method of treating cancer comprising administering by administering a PAR-4 agonist as part of a cancer treatment regimen. In some instances the PAR-4 agonist is non-steroidal anti-inflammatory drug, for instance ketorolac, or a pharmaceutically acceptable salt or ester thereof. The cancer treatment regimen can include administration of one or more additional PAR-4 agonists, one or more additional chemotherapeutic agents, exposure to ionizing radiation, and/or surgical interventions.

According to an aspect of the present invention, there is provided a method of treating cancer comprising administering ketorolac, or a pharmaceutically salt or ester thereof, in combination with one or more additional chemotherapeutic agents, in which the additional chemotherapeutic agents are administered with ketorolac either simultaneously, sequentially, or separately.

According to one aspect of the present invention, there is provided a method of treating renal cell carcinoma (RCC) comprising administration of non-steroidal anti-inflammatory drugs such as ketorolac, or a pharmaceutically acceptable salt or ester thereof.

According to another aspect of the present invention, there is provided a pharmaceutical composition comprising ketorolac, or a pharmaceutically acceptable salt or ester thereof, with one or more pharmaceutically acceptable excipients for the treatment of renal cell carcinoma (RCC).

According to another aspect of the present invention, there is provided a method of treating renal cell carcinoma (RCC) by administration of ketorolac, or a pharmaceutically acceptable salt or ester thereof, in combination with one or more additional cancer treatment regimens. The cancer treatment regimen can include administration of one or more additional therapeutic agents, exposure to ionizing radiation, and/or surgical interventions.

According to another aspect of the present invention, there is provided a use of ketorolac, or a pharmaceutically acceptable salt thereof, in combination with one or more therapeutic agents either simultaneously, sequentially, or separately for the treatment of renal cell carcinoma (RCC). In some instances, the therapeutic agent can include one or more chemotherapeutic drugs.

According to another aspect of the present invention, there are provided pharmaceutical compositions and kits including ketorolac, or a pharmaceutically acceptable salt or ester thereof, and at least one other therapeutic agent.

The details of one or more embodiments are set forth in the descriptions below. Other features, objects, and advantages will be apparent from the description and from the claims.

DETAILED DESCRIPTION

Figure 1:
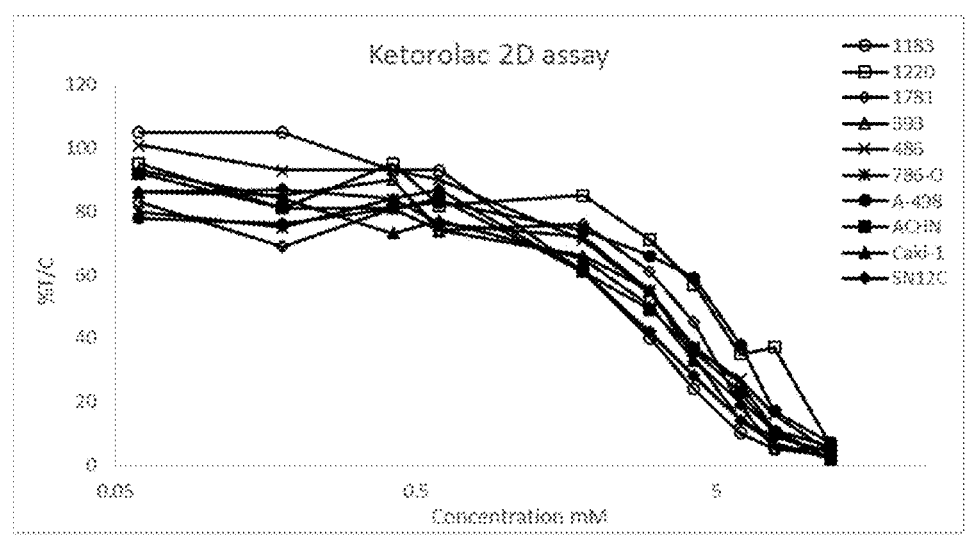
FIG. 1 depicts in vitro activity of ketorolac against various renal cell carcinoma cell lines.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

Ketorolac is an officially adopted name for the compound (±)-5-benzoyl-2,3-dihydro-1H-pyrrolizine-1-carboxylic acid), a nonsteroidal anti-inflammatory drug (NASID). Ketorolac has been used for the management of moderate to severe acute pain. Ketorolac has the following chemical structure:

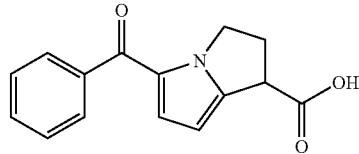 [SMILES: O=C(c1ccccc1)c1ccc2n1CCC2C(=O)O]

As used herein, term "ketorolac" is denoted in broad sense to include not only ketorolac per se but also its pharmaceutically acceptable derivatives. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable polymorphs, pharmaceutically acceptable prodrugs, pharmaceutically acceptable tautomers, pharmaceutically acceptable complexes etc.

Ketorolac may be formulated as a pharmaceutically acceptable salt. Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made. In some embodiments, ketorolac can be formulated as an ammonium salt, such as 2-amino-2-(hydroxymethyl)-1,3-propanediol (1:1); this salt is commercially available under the name Toradol.

Ketorolac may be formulated as pharmaceutically acceptable ester. Esters can substantially increase the bioavailability of the compounds, permitting more effective oral therapy. In some embodiments, the ester is a $C_1$-$C_{10}$ alkyl ester of the 1-carboxylic acid, which may or may not be substituted. A preferred substituent is carbonyl-oxy and alkyloxy-carbonyloxy. Exemplary esters include methyl, ethyl, 2-morpholinylethyl, pivaloyloxy-methyl ester, 1-(isopropyloxy-carbonyloxy)ethyl ester, and 1-(acetyloxy)ethyl ester.

Unchecked cell growth is a characteristic of all cancers. Suppression of growth inhibitory or apoptotic functions by growth stimulatory or cell survival proteins is seen in human cancer. The coupling between cell division and cell death is thought to act as a barrier that cells must overcome for cancer initiation and progression. This may be the underlying reason why cancer cells often over express anti-apoptotic proteins such as Bcl-2, Bcl-xL and survivin, along with inactivation of pro-apoptotic tumor-suppressor proteins p53, p19arf, PAR-4 and PTEN that control apoptosis pathways, generating severe defects in the balance between cell division and programmed cell death in cancer settings. Thus the mentioned abnormalities that generate defects in apoptotic pathways allow cancer cells to survive.

The inventors of the present invention have surprisingly found that ketorolac is a potent secretor or agonist of prostate apoptosis response-4 (PAR-4). As such, ketorolac can be used to treat PAR-4 suceptible cancers, either alone or in combination with other cancer therapy regimens.

The terms "induces, "secretor" or "agonist" are used interchangeably throughout the specification, all the terms indicate that the drug increases the expression of PAR-4.

The term "combination" as used herein, defines either a fixed combination in one unit dosage form, a non-fixed combination or a kit of parts for the combined administration.

The term "treating" or "treatment" as used herein comprises a method for relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease.

PAR-4 is a pro-apoptotic, tumor suppressor protein. It is found to be deregulated in several cancers. Several studies have documented the association of low level of PAR-4 with poor prognosis in cancers of prostate, endometrial, renal, pancreas, and breast. Endoplasmic reticulum-stress and higher levels of protein kinase A in tumor cells confer the coveted feature of cancer selective response to extracellular and intracellular PAR-4, respectively. Recent studies have shown that systemic PAR-4 confers resistance to tumor growth in mice.

PAR-4 is a leucine zipper domain protein identified in cells undergoing apoptosis in response to exogenous insults. PAR-4 is expressed ubiquitously among the various tissue types, and resides in both the cytoplasm and the nucleus. Although endogenous PAR-4 is largely inactivated, and does not produce extensive apoptosis by itself, it is essential for the apoptotic function of diverse cytotoxic agents. Interestingly, PAR-4 over-expression is sufficient to induce apoptosis in most cancer cells, but not in normal or immortalized cells.

PAR-4 has been shown to activate apoptosis through intrinsic and extrinsic pathways. Upregulation or induction of PAR-4 by apoptotic stimuli such as tumor necrosis factor alpha (TNFα), TRAIL and Fas induce cell death in cancer cells. Other studies showed that overexpression of PAR-4 enhances the activity of anticancer drugs such as 5-fluorouracil and induces radio-sensitivity. While the intracellular role of PAR-4 is established and the mechanisms well studied, recent studies have demonstrated that secretory or extracellular PAR-4 induces apoptosis in cancer cells.

Previous studies suggest that the role of PAR-4 in apoptosis is cancer cell selective in that (i) overexpression of PAR-4 triggers apoptosis in various cancer cell lines but not in normal and primary cells, (ii) depletion of PAR-4 by RNA interference (RNAi) confers resistance in cancer cells, but not in primary fibroblasts, to various apoptotic agents, and (iii) PAR-4 displays proapoptotic functions in cells transformed with oncogene Ras but not in normal cells. Recently, PAR-4 was shown to be secreted by mammalian cells and, through interaction with the cell surface receptor GRP78, to induce cancer cell apoptosis in a specific manner.

PAR-4 is found to be down regulated in several cancers like prostate, endometrial, renal, pancreas, and breast. Also because the baseline levels of PAR-4 secreted by normal cells are generally inadequate to cause massive apoptosis in cancer cell, secretogogues that bolster the release of PAR-4 constitute an important therapeutic advance. For example, Nutlin-3a, originally developed as an MDM2 inhibitor, stimulated PAR-4 secretion at micromolar levels in mouse embryonic fibroblast (MEF) cells.

The inventors of the present invention have surprisingly found through various studies that ketorolac increases the secretion of PAR-4 protein.

The types of cancers which may be treated using PAR-4 agonists include: acute lymphoblastic leukemia (ALL), acute myeloid leukemia (AML), cancer in adrenocortical carcinoma, adrenal cortex cancer, AIDS-related cancers, Kaposi sarcoma, AIDS-related lymphoma, primary CNS lymphoma, anal cancer, appendix cancer, carcinoid tumors, astrocytomas, atypical teratoid/rhabdoid tumor, basal cell carcinoma, skin cancer (nonmelanoma), bile duct cancer, extrahepatic bladder cancer, bladder cancer, bone cancer (includes Ewing sarcoma and osteosarcoma and malignant fibrous histiocytoma), brain tumors, breast cancer, bronchial tumors, Burkitt lymphoma (non-Hodgkin), carcinoid tumor, cardiac (heart) tumors, atypical teratoid/rhabdoid tumor, embryonal tumors, germ cell tumors, lymphoma, primary—cervical cancer, cholangiocarcinoma, chordoma, chronic lymphocytic leukemia (CLL), chronic myelogenous leukemia (CIVIL), chronic myeloproliferative neoplasms, colorectal cancer, colorectal cancer, craniopharyngioma, cutaneous T-cell lymphoma, ductal carcinoma in situ (DCIS), embryonal tumors, central nervous system, endometrial cancer, ependymoma, esophageal, esthesioneuroblastoma, ewing sarcoma, extracranial germ cell tumor, extragonadal germ cell tumor, eye cancer, intraocular melanoma, retinoblastoma, fallopian tube cancer, fibrous histiocytoma of bone, malignant, and osteosarcoma, gallbladder cancer, gastric (stomach) cancer, gastric (stomach) cancer, gastrointestinal carcinoid tumor, gastrointestinal stromal tumors (GIST), gastrointestinal stromal tumors (GIST), germ cell tumors, central nervous system, extracranial, extragonadal, ovarian testicular, gestational trophoblastic disease, gliomas, hairy cell leukemia, head and neck cancer, heart tumors, hepatocellular (liver) cancer, histiocytosis, Langerhans Cell, Hodgkin's lymphoma, hypopharyngeal cancer, intraocular melanoma, islet cell tumors, pancreatic neuroendocrine tumors, Kaposi sarcoma, kidney—langerhans cell histiocytosis, laryngeal cancer, laryngeal cancer and papillomatosis, leukemia, lip and oral cavity cancer, liver cancer (primary), lung cancer, lung cancer, lymphoma—macroglobulinemia, Waldenström-Non-Hodgkin lymphoma, male breast cancer, malignant fibrous histiocytoma of bone and osteosarcoma, melanoma, intraocular (eye), Merkel cell carcinoma, mesothelioma, malignant, mesothelioma, metastatic squamous neck cancer with occult primary, midline tract carcinoma involving NUT gene, mouth cancer, multiple endocrine neoplasia syndromes, multiple myeloma/plasma cell neoplasms, mycosis fungoides, myelodysplastic syndromes, myelodysplastic/myeloproliferative neoplasms and chronic myeloproliferative neoplasms, myelogenous leukemia, chronic (CML), myeloid leukemia, acute (AML), nasal cavity and paranasal sinus cancer, nasopharyngeal cancer, nasopharyngeal cancer, neuroblastoma, non-hodgkin lymphoma, non-small cell lung cancer, oral cancer, lip and oral cavity cancer and oropharyngeal cancer, osteosarcoma and malignant fibrous histiocytoma of bone, ovarian cancer, pancreatic cancer and pancreatic neuroendocrine tumors (islet cell tumors), papillomatosis, paraganglioma, paraganglioma, paranasal sinus and nasal cavity cancer, parathyroid cancer, penile cancer, pharyngeal cancer, pheochromocytoma, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, renal cell (kidney) cancer, retinoblastoma, rhabdomyosarcoma, salivary gland cancer, salivary gland tumors, Ewing sarcoma, Kaposi sarcoma, osteosarcoma, rhabdomyosarcoma, uterine sarcoma, vascular tumors, Sézary syndrome, skin cancer, small cell lung cancer, small intestine cancer, soft tissue sarcoma, squamous cell carcinoma, squamous neck cancer with occult primary, metastatic, stomach (gastric) cancer, stomach (gastric) cancer, T-cell lymphoma, cutaneous, testicular cancer, throat cancer, thymoma and thymic carcinoma, thyroid cancer, ureter and renal pelvis, transitional cell cancer, urethral cancer, uterine cancer, endometrial and uterine sarcoma, vaginal cancer, vaginal cancer, vascular tumors, vulvar cancer, Waldenström Macroglobulinemia, and Wilms Tumor. Such cancers can be designated PAR-4 susceptible cancers.

In certain preferred embodiments, ketorolac can be used to treat prostate cancer, breast cancer, lung cancer, or skin cancer/melanoma. In particular, ketorolac can be used to treat superficial spreading melanoma, nodular melanoma, lentigno maligna melanoma, and desmoplastic melanoma.

The inventors have also surprisingly found to ketorolac can be used to treat renal cell carcinoma, either through PAR-4-related or PAR-4-unrelated pathways According to the present invention there is provided a pharmaceutical composition comprising ketorolac with one or more pharmaceutically acceptable excipients for the treatment of renal cell carcinoma (RCC).

Ketorolac can be administered according to various dosing regimens. For instance, ketorolac can be administered once a day, twice a day, three times per day, or even more than three times a day. Ketorolac can be administered such that the total daily dose is at least 50 mg, at least 100 mg, at least 250 mg, at least 500 mg, at least 750 mg, at least 1,000 mg, at least 1,250 mg, at least 1,500 mg, at least 1,750 mg, or at least 2,000 mg. In some instances, the total daily dose can be from 5-5,000 mg, 10-5,000 mg, 25-5,000 mg, 50-5,000 mg, 100-5,000 mg, 200-2,500 mg, 500-2,500 mg, 10-2,500 mg, 50-2,500 mg, 100-2,500 mg, 100-2,000 mg, 250-2,000 mg or 500-2,000 mg. In other embodiments, ketorolac can be administered less than once daily, instance, once every two days, once every three days, once every five days, once every seven days, once every ten days, once every fourteen days, once every twenty-eight days or once every month.

In some instances, ketorolac can be administered intermittently, for instance for a period of 1-10 days, followed by a period in which no ketorolac is administered (e.g., 1-10 days), followed by another period e.g., 1-10 days, in which ketorolac is administered. The on/off dosing schedule can be repeated as many times as necessary.

Preferably, ketorolac may be provided in the form of a pharmaceutical composition such as, but not limited to, solid unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution and sprinkles, however, other dosage forms such as controlled release formulations, lyophilized formulations, modified release formulations, delayed release formulations, extended release formulations, pulsatile release formulations, dual release formulations and the like may fall within the scope of the invention. Apart from this, it will be well acknowledged by person skilled in the art to have other forms of pharmaceutical compositions like liquid or semisolid dosage form (liquids, suspensions, solutions, dispersions, ointments, creams, emulsions, microemulsions, sprays, spot-on), injection/parenteral preparations, topical, inhalations, buccal, nasal etc. and which may be envisaged under the ambit of the invention.

Depending on the pathological stage, patient's age and other physiological parameters, size of the tumor, and the extent of invasion, the pharmaceutical composition comprising ketorolac may require specific dosage amounts and specific frequency of administrations. Preferably, on an average, the dose range that may be feasible for producing suitable anticancer effect may range from 25 mg to 3gms depending on the above factors, and the route of administration adopted for administering the pharmaceutical composition. The dosing frequency that may be required for adherence to the therapy may be at least once, twice or thrice a day depending on the above mentioned factors and the route of administration adopted for administering the pharmaceutical composition.

It will further be well acknowledged by person skilled in the art that by specific treatment with ketorolac, various physicochemical properties could be improved such as solubility, better absorption, bioavailability, increased shelf life, etc. and wherein such specific treatment refers to one or more of micronization and nanosizing techniques which may achieve one or more of the benefits aimed hereinabove, and may also assist in dose reduction. For instance, ketorolac may be present in the form of nanoparticles which have an average particle size of less than 2,000 nm, less than 1,500 nm, less than 1,000 nm, less than 750 nm, less than 500 nm, or less than 250 nm.

Suitable pharmaceutically acceptable excipients may be used for formulating the dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, surface stabilizers, channeling agents, coating agents or combinations thereof.

The present inventors have discovered the ketorolac is surprisingly effective for the treatment of renal cell carcinoma. In certain embodiments, ketorolac can be used to treat conventional (clear-cell) renal cell carcinoma, papillary renal cell-carcinoma, chromophobe renal carcinoma, oncocytoma, or collecting-duct carcinoma. Renal cell carcinoma can be classified in stages, according to the extent of disease progression. The TNM (tumor size/lymph node/metastasis) system includes the following stages of RCC:

Stage I: Tumor of a diameter of 7 cm (approx. 2¾ inches) or smaller, and limited to the kidney, with no lymph node involvement or metastases to distant organs.

Stage II: Tumor larger than 7.0 cm but still limited to the kidney, with no lymph node involvement or metastases to distant organs.

Stage III: Tumor of any size with involvement of a nearby lymph node but no metastases to distant organs. Tumor of this stage may be with or without spread to fatty tissue around the kidney, with or without spread into the large veins leading from the kidney to the heart; or Tumor with spread to fatty tissue around the kidney and/or spread into the large veins leading from the kidney to the heart, but without spread to any lymph nodes or other organs; or Tumor with spread to fatty tissue around the kidney and/or spread into the large veins leading from the kidney to the heart, but without spread to any lymph nodes or other organs.

Stage IV: Tumor that has spread directly through the fatty tissue and the fascia ligament-like tissue that surrounds the kidney; or involvement of more than one lymph node (near or distant from kidney); or distant metastases, such as in the lungs, bone, or brain.

Ketorolac can be used to treat Stage I RCC, Stage II RCC, Stage III RCC, or Stage IV RCC. In some embodiments, ketorolac can reduce tumor size, inhibit tumor growth, alleviate symptoms, delay progression, prolong survival, including, but not limited to disease free survival, prevent or delay RCC metastasis, reduce or eliminate preexisting RCC metastasis, and/or prevent recurrence of RCC. All of these effects fall within the general scope of treating RCC.

As used herein, the term "delay" refers to methods that reduce the probability of disease development/extent in a given time frame, when compared to otherwise similar methods that do not include the use of ketorolac. Probabilities can be established using clinical trials, but can also be determined using in vitro assays when correlations have been established. In some embodiments, ketorolac can inhibit renal cancer cell proliferation. For instance, at least about 10%, 20%, 30%, 40%, 60%, 70%, 80%, 90%, or 100% of cell proliferation is inhibited. In some embodiments, ketorolac can inhibit renal cancer metastasis. For instance, at least about 10%, 20%, 30%, 40%, 60%, 70%, 80%, 90%, or 100% of metastasis is inhibited.

According to the present invention, there is provided a method of alleviating or treating renal cell carcinoma (RCC) or PAR-4 susceptible cancers by administration of ketorolac in combination with one or more anti-cancer drugs either simultaneously, sequentially, or separately. In certain embodiments, ketorolac can be administered with:

(A) cytotoxic anti-neoplastic drugs such as nucleoside analogues, antifolates, antimetabolites, topoisomerase I inhibitor, anthracyclines, podophyllotoxins, taxanes, vinca alkaloids, alkylating agents, platinum compounds, proteasome inhibitors, nitrogen mustards & oestrogen analogue; and/or (B) targeted anti-neoplastic drugs such as monoclonal antibodies, tyrosine kinase inhibitors, mTOR inhibitors, retinoids, immunomodulatory agents, histone deacetylase inhibitors, other kinase inhibitors.

For the treatment of either renal cell carcinoma or PAR-4 agonist susceptible cancers, ketorolac may be administered (simultaneously, sequentially or separately) with one or more anti-cancer drugs. Such drugs include small molecule chemical agents and biological agents, including immunotherapies. Examplary anti-cancer drugs include Abiraterone acetate, Methotrexate, Paclitaxel Albumin-stabilized Nanoparticle, Brentuximab Vedotin, Ado-Trastuzumab Emtansine, Doxorubicin Hydrochloride, Afatinib Dimaleate, Everolimus, Netupitant, Palonosetron Hydrochloride, Imiquimod, Aldesleukin, Alectinib, Alemtuzumab, Melphalan Hydrochloride, Melphalan, Pemetrexed Disodium, Chlorambucil, Aminolevulinic acid, Anastrozole, Aprepitant, Pamidronate Disodium, Exemestane, Nelarabine, Arsenic Trioxide, Ofatumumab, Asparaginase *Erwinia chrysanthemi*, Atezolizumab, Bevacizumab, Axitinib, Azacitidine, Carmustine, Belinostat, Bendamustine hydrochloride, Bevacizumab, Bexarotene, Tositumomab, Bicalutamide, Bleomycin, Blinatumomab, Blinatumomab, Bortezomib, Bosutinib, Busulfan, Cabazitaxel, Cabozantinib, Alemtuzumab, Irinotecan hydrochloride, Capecitabine, Fluorouracil, Carboplatin, Carfilzomib, Bicalutamide, Lomustine, Ceritinib, Daunorubicin Hydrochloride, Cetuximab, Chlorambucil, Cyclophosphamide, Clofarabine, Cobimetinib, Dactinomycin, Cobimetinib, Crizotinib, Ifosfamide, Ramucirumab, Cytarabine, Dabrafenib, Dacarbazine, Decitabine, Daratumumab, Dasatinib, Daunorubicin hydrochloride, Decitabine, Efibrotide Sodium, Defibrotide sodium, Degarelix, Denileukin Diftitox, Denosumab, Dexamethasone, Dexrazoxane hydrochloride, Dinutuximab, Docetaxel, Doxorubicin Hydrochloride, Dacarbazine, Rasburicase, Epirubicin hydrochloride, Elotuzumab, Oxaliplatin, Eltrombopag olamine, Aprepitant, Elotuzumab, Enzalutamide, Epirubicin Hydrochloride, Cetuximab, Eribulin Mesylate, Vismodegib, Erlotinib hydrochloride, Etoposide, Raloxifene hydrochloride, Melphalan hydrochloride, Toremifene, Panobinostat, Fulvestrant, Letrozole, Filgrastim, Fludarabine phosphate, Flutamide, Methotrexate, Pralatrexate, Recombinant HPV Quadrivalent Vaccine, Recombinant HPV Nonavalent vaccine, Obinutuzumab, Gefitinib, Gemcitabine hydrochloride, Gemtuzumab Ozogamicin, Afatinib Dimaleate, Imatinib Mesylate, Glucarpidase, Goserelin acetate, Eribulin mesylate, Trastuzumab, Topotecan hydrochloride, Palbociclib, Ibritumomab tiuxetan, Ibrutinib, Ponatinib hydrochloride, Idarubicin hydrochloride, Idelalisib, Imiquimod, Axitinib, Recombinant Interferon Alfa-2b, Tositumomab, Ipilimumab, Gefitinib, Romidepsin, Ixabepilone, Ixazomib Citrate, Ruxolitinib phosphate, Cabazitaxel, Ado-Trastuzumab Emtansine, Palifermin, Pembrolizumab, Lanreotide Acetate, Lapatinib ditosylate, Lenalidomide Lenvatinib mesylate, Leuprolide acetate, Olaparib, Vincristine Sulfate, Procarbazine hydrochloride, Mechlorethamine hydrochloride, Megestrol Acetate, Trametinib, Mercaptopurine, Temozolomide, Mitoxantrone hydrochloride, Plerixafor, Busulfan, Azacitidine, Gemtuzumab Ozogamicin, Vinorelbine tartrate, Necitumumab, Nelarabine, Sorafenib tosylate, Nilotinib, Ixazomib citrate, Nivolumab, Romiplostim, Obinutuzumab, Ofatumumab, Olaparib, Omacetaxine mepesuccinate, Pegaspargase, Ondansetron hydrochloride, Osimertinib, Panitumumab, Panobinostat, Peginterferon Alfa-2b, Pembrolizumab, Pertuzumab, Plerixafor, Pomalidomide, Ponatinib hydrochloride, Necitumumab, Pralatrexate, Procarbazine hydrochloride, Aldesleukin, Denosumab, Ramucirumab, Rasburicase, Regorafenib, Lenalidomide, Rituximab, Rolapitant hydrochloride, Romidepsin, Ruxolitinib phosphate, Siltuximab, Dasatinib, Sunitinib malate, Thalidomide, Dabrafenib, Osimertinib, Talimogene, Atezolizumab, Temsirolimus, Thalidomide, Dexrazoxane hydrochloride, Trabectedin, Trametinib, Trastuzumab, Lapatinib ditosylate, Dinutuximab, Vandetanib, Rolapitant hydrochloride, Bortezomib, Venetoclax, Crizotinib, Enzalutamide, Ipilimumab, Trabectedin, Ziv-Aflibercept, Idelalisib, Ceritinib, and pharmaceutically acceptable salts thereof.

In some embodiments, ketorolac can be administered with one or more tyrosine kinase inhibitors. Exemplary tyrosine kinase inhibitors include dasatinib, erlotinib, gefitinib, imatinib, lapatinib, nilotinib, sorafenib, and sunitinib. These inhibitors are typically formulated as pharmaceutically acceptable salts. A preferred tyrosine kinase inhibitor that can be used with ketorolac is sunitinib malate.

Ketorolac can be administered with one or more chemotherapeutic agents either simultaneously, sequentially, or separately. In certain cases, ketorolac can be administered for a period of at least 1 week, at least 2 weeks, at least 4 week, at least 6 weeks, at least 8 week, or at least 10 weeks, prior to commencing treatment with additional agents. In some instances, ketorolac and the other agent can be administered intermittently, for instance a period of ketorolac administration, followed by a period in which the other agent to administered, followed by another period of ketorolac administration. The cycle can be repeated as many times as necessary.

In certain cases, the combination of ketorolac and additional agent will exhibit a greater than additive effect (i.e., a synergistic effect). In other instance, the use of ketorolac permits a reduced amount of the other agent to be administered, without a corresponding decrease in therapeutic efficiency.

In cases of combination therapy, it is possible that a unitary dosage form comprising both ketorolac and one or more additional anti-cancer drugs may be employed. In some instances, the combinations may be provided in form of kit preparation wherein ketorolac is present in an oral or parenteral composition and the additional anti-cancer drug therapy may be provided in an oral or parenteral composition. In one embodiment, the kit preparation may be provided in an all oral dosage form presentation wherein both the ketorolac and the additional anti-cancer drug are presented in an oral dosage form. In another embodiment, the kit preparation may be provided as an oral plus parenteral dosage form presentation wherein ketorolac is presented in an oral form and the additional anti-cancer drug is presented in a parenteral form. Alternatively, the kit preparation may be provided wherein ketorolac is presented in a parenteral form and the additional anti-cancer drug is presented in an oral dosage form.

In some instances, ketorolac can be used in combination with ionizing radiation and/or surgical interventions for the treatment of cancer, for instance renal cell carcinoma. Ketorolac can be administered before, during, or after treatment with ionizing radiation or surgical intervention. In certain cases, ketorolac can be administered for a period of at least 1 week, at least 2 weeks, at least 4 week, at least 6 weeks, at least 8 week, or at least 10 weeks, prior to commencing treatment with ionizing radiation or surgery. Exemplary forms of radiation include x-rays, gamma rays, electron beams and proton beams. It has been found that administration of ketorolac permits a reduction in the total exposure of the patient to ionizing radiation, without a corresponding reduction in therapeutic efficiency. In certain instances, ketorolac can be administered both prior and subsequent to ionizing radiation and/or surgical interventions. For instance, ketorolac can be administered for a period of at least 1 week, at least 2 weeks, at least 4 week, at least 6 weeks, at least 8 week, or at least 10 weeks, following treatment with ionizing radiation or surgery.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

In vitro 2D Assay

The objective of this study was to investigate the in-vitro anticancer activity of ketorolac. Antitumor activity was assessed in ten selected renal cancer cell lines by using the CellTiter-Blue Cell Viability Assay. The human renal cancer cell lines RXF 1183L, RXF 1220L, RXF 1781L, RXF 393L, RXF 486L, RXF 786-0, RXF A-498, RXF ACHN, RXF Caki-1 and RXF SN12C were used. RXF 1183L, RXF 1220L, RXF 1781L, RXF 393L and RXF 486L were established at Oncotest from the corresponding human patient-derived xenograft. The cell lines 786-0, A-498, Caki-1 and SN12C were purchased from NCI (National Cancer Institute, Bethesda, Md., USA). ACHN was purchased from ECACC (European Collection of Cell Cultures, Salisbury, UK). Authenticity of cell lines was confirmed at the DSMZ by STR (short tandem repeat) analysis, a PCR based DNA-fingerprinting methodology.

Cell lines were routinely passaged once or twice weekly and maintained in culture for up to 20 passages. All cells were grown at 37° C. in a humidified atmosphere with 5% $CO_2$ in RPMI 1640 medium (25 mM HEPES, with L-glutamine, #FG1385, Biochrom, Berlin, Germany) supplemented with 10% (v/v) fetal calf serum (Sigma, Taufkirchen, Germany) and 0.1 mg/mL gentamicin (Life Technologies, Karlsruhe, Germany).

Ketorolac was dissolved at a concentration of 60 mM in cell culture media. Starting with this stock solution, dilutions were made using cell culture media resulting in final test concentrations of 12000, 7800, 6000, 4200, 3000, 1800, 600, 420, 180, 60 µM. Precipitation was not observed.

The CellTiter-Blue Cell Viability Assay was used according to manufacturer's instructions. Briefly, cells were harvested from exponential phase cultures, counted and plated in 96-well flat-bottom microtiter plates at a cell density of 4,000-12,000 cells/well depending on the cell line's growth rate. After a 24 h recovery period to allow the cells to resume exponential growth, ketorolac was applied at 8 to 10 concentrations in duplicate and treatment continued for 96 h. After 96 h treatment of cells, 20 µL/well CellTiter-Blue® reagent was added. Following an incubation period of up to four hours, fluorescence (FU) was measured by using the Enspire Multimode Plate Reader (excitation λ=531 nm, emission λ=615 nm).

For calculations, the mean values of duplicate/quadruplicate (untreated control) data were used. Sigmoidal concentration-response curves were fitted to the data points (T/C values) obtained for each cell line using 4 parameter non-linear curve fit.

Concentration-dependent activity with sigmoidal concentration-effect curves was detected in both runs in all cell lines tested. Individual $IC_{50}$ values were in the range of 2404 µM (RXF 1183L) and 4775 µM (RXF 1220L) (FIG. 1).

| Cell line | Absolute $IC_{50}$ µM | Relative $IC_{50}$ µM |
|---|---|---|
| 1183 | 2404 | 2668 |
| 1220 | 4775 | 5356 |
| 1781 | 3824 | 4438 |
| 393 | 3142 | 3753 |
| 486 | 3147 | 3291 |
| 786-O | 3251 | 3848 |
| A-498 | 4745 | 5653 |
| ACHN | 2797 | 3393 |
| Caki-1 | 2794 | 3441 |
| SN12C | 2444 | 2825 |
| Geometric mean | 3241 | 3757 |

Example 2

In vitro 3D Assay

Ketorolac was characterized for its ability to inhibit anchorage independent growth and ex vivo colony formation of tumor cells in semi-solid medium. The compound was tested against 10 human tumor xenograft-derived cell suspensions or tumor cell lines of renal cancer. Test concentrations ranged from 0.2794 mM to 12 mM.

Figure 2:
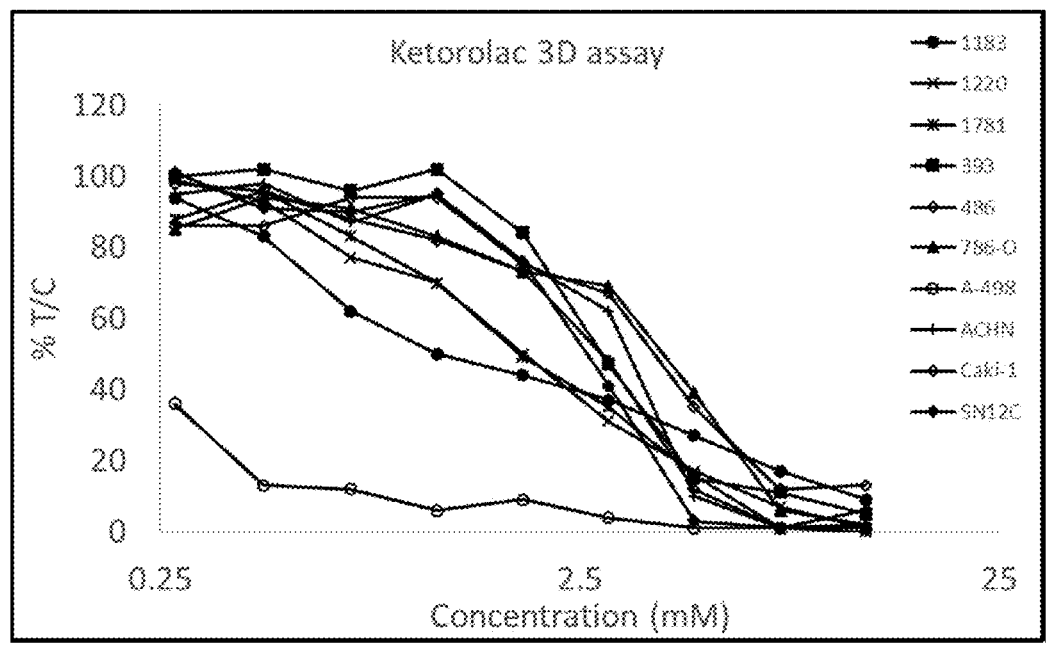
FIG. 2 depicts absolute IC50 values in human tumor models treated with ketorolac.

Ketorolac inhibited colony formation in a concentration-dependent manner with a mean relative $IC_{50}$ value of 2,043 µM. Bottom plateaus of the concentration-effect curves of responding tumor models were in the range from 0 to 18%, indicating clear inhibition of tumor colony growth in the selected test range. Based on relative $IC_{50}$ values, pronounced activity was observed for ketorolac against A-498 cells ($IC_{50}$=279 µM) (FIG. 2).

| Cell line | Absolute $IC_{50}$ µM | Relative $IC_{50}$ µM |
|---|---|---|
| 1183 | 1552 | 1488 |
| 1220 | 1766 | 1748 |
| 1781 | 1899 | 2035 |
| 393 | 2826 | 2726 |
| 486 | 2677 | 2611 |
| 786-O | 3841 | 4201 |
| A-498 | 279 | 279 |
| ACHN | 3138 | 3254 |
| Caki-1 | 3676 | 3754 |
| SN12C | 2594 | 2643 |
| Geometric mean | 2043 | 2083 |

Example 3

Clonogenic Assay

Cell lines were routinely passaged one or twice weekly. All cells were grown at 37° C. in a humidified atmosphere with 5% $CO_2$ in RPMI 1640 medium (Biochrom) supplemented with 10% (v/v) fetal calf serum and 0.1 mg/mL gentamicin. The percentage of viable cells was determined in a Neubauer-hemocytometer using trypan blue exclusion.

Tumor xenografts (patient-derived, as well as cell line-derived xenografts) were passaged as subcutaneous xenografts in NMRI nu/nu mice. At a tumor volume of 400-1000 $mm^3$ tumor-bearing mice were sacrificed and tumors were collected under sterile conditions without delay according to the relevant Oncotest SOPs and the relevant animal welfare guidelines published by the FELASA and the GV-SOLAS. Tumors were mechanically disaggregated and subsequently incubated with an enzyme cocktail consisting of collagenase type IV (41 U/mL), DNase I (125 U/mL), hyaluronidase type III (100 U/mL), and dispase II (1.0 U/mL) in RPMI 1640 medium (Life Technologies) at 37° C. for 60-120 minutes. Cells were passed through sieves of 100 µm and 40 µm mesh size (Cell Strainer, BD Falcon™), and washed with RPMI 1640 medium. The percentage of viable cells was determined in a Neubauer-hemocytometer using trypan blue exclusion. Aliquots of the cells were frozen down, and stored in liquid nitrogen. On each day of an experiment, a frozen aliquot of tumor cells was thawed and used for preparation of assay plates.

The clonogenic assay was carried out in a 96 well plate format using ultra low attachment plates. For each test, cells were prepared as described above and assay plates were prepared as follows: each test well contained a layer of semi-solid medium with tumor cells (50 µL), and a second layer of medium supernatant with or without test compound (100 The cell layer consisted of $2.5 \times 10^3$ to $1 \times 10^4$ tumor cells per well, which were seeded in 50 µL/well cell culture medium (IMDM, supplemented with 20% (v/v) fetal calf serum, 0.01% (w/v) gentamicin, and 0.4% (w/v) agar). After 24 hours ketorolac was added after serial dilution in cell culture medium, and left on the cells for the duration of the experiment (continuous exposure, 100 µl drug overlay). Every plate included six untreated control wells and drug-treated groups in duplicate at 9 concentrations. Cultures were incubated at 37° C. and 7.5% $CO_2$ in a humidified atmosphere for 8 to 13 days and monitored closely for colony growth using an inverted microscope. Within this period, ex vivo tumor growth led to the formation of colonies with a diameter of >50 µm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 μl/well).

Ketorolac inhibited colony formation in a concentration-dependent manner with a mean relative $IC_{50}$ value of 2,083 μM (2,043 μM). Bottom plateaus of the concentration-effect curves of the responding tumor models were in the range from 0 to 18%, indicating clear inhibition of tumor colony growth in the selected test range. Based on relative $IC_{50}$ values, pronounced activity was observed for ketorolac against A-498 cells ($IC_{50=279}$ μM).

Example 4

In vitro 3D Combination Studies

The objective of this study was to assess anti-tumor efficacy of ketorolac in combination with sunitinib in a 5×5 matrix combination format against tumor cell lines of renal cancer using a clonogenic assay with image analysis as read-out. The Bliss independence methodology was used for data analysis, in order to identify possible synergistic effects.

The clonogenic assay was carried out in a 96 well plate format using ultra low attachment plates. For each test cells were prepared as described above, and assay plates were prepared as follows: each test well contained a layer of semi-solid medium with tumor cells (50 μl), and a second layer of medium supernatant with or without test compounds (100 μl). The cell layer consisted of $3\times10^3$ to $1\times10^4$ tumor cells per well, which were seeded in 50 μl/well cell culture medium (IMDM, supplemented with 20% (v/v) fetal calf serum, 0.01% (w/v) gentamicin, and 0.4% (w/v) agar). The soft agar layer was immediately covered with 90 μl of the same culture medium without agar. After 24 h the test compounds were added after serial dilution in IMDM and transfer in cell culture medium, and left on the cells for the duration of the experiment (continuous exposure, 100 μL total drug overlay). Every plate included six untreated control wells and drug-treated groups in a layout as shown above. Cultures were incubated at 37° C. and 7.5% $CO_2$ in a humidified atmosphere for 8 or 13 days and monitored closely for colony growth using an inverted microscope. Within this period, ex vivo tumor growth led to the formation of colonies with a diameter of >50 μm. At the time of maximum colony formation, counts were performed with an automatic image analysis system (CellInsight NXT, Thermo Scientific). 48 hours prior to evaluation, vital colonies were stained with a sterile aqueous solution of 2-(4-iodophenyl)-3-(4-nitrophenyl)-5-phenyltetrazolium chloride (1 mg/ml, 100 μl/well).

Ketorolac alone inhibited colony formation of tumor cells seeded in soft agar in a concentration-dependent manner with relative $IC_{50}$ values ranging from 588.63 μM to 1758.21 μM. Sunitinib was active with relative $IC_{50}$ values ranging from 1.5 μM to 4.593 μM. Overall, synergistic effects were observed for the combination of ketorolac with sunitinib in the renal cancer cell line RXF A-498. Additive effects were observed for the combination of ketorolac with sunitinib in the cell line RXF 1183L.

Figure 3:
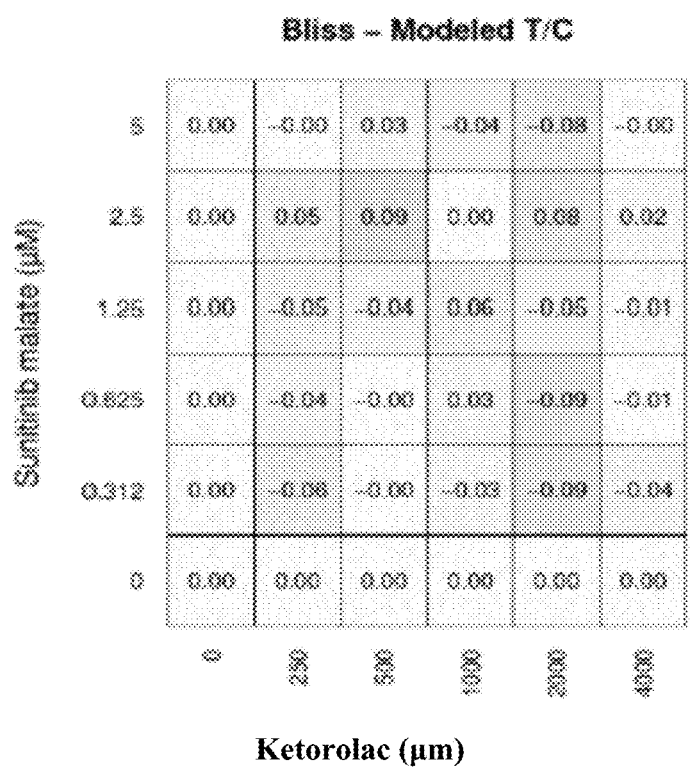
FIG. 3 depicts anti-tumor efficacy of ketorolac in combination with sunitinib in RXF 1183L. Positive values (Bliss Index ≥0.15) indicate synergism, negative values (Bliss Index ≤−0.15) indicate antagonism, and zero is the neutral value.
Figure 4:
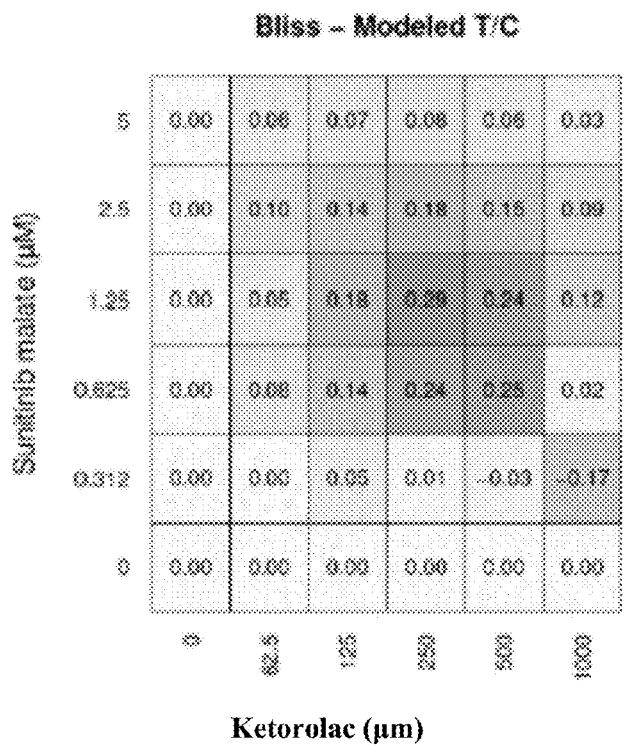
FIG. 4 depicts anti-tumor efficacy of ketorolac in combination with sunitinib in RXF A-498. Positive values (Bliss Index ≥0.15) indicate synergism, negative values (Bliss Index ≤−0.15) indicate antagonism, and zero is the neutral value.

Ketorolac and sunitinib inhibited colony formation of RXF 1183L cells seeded in soft agar in a concentration-dependent manner. This is also reflected in the matrix combination, where activity of the different combinations was observed with increasing test concentrations of both compounds. Bliss independence analysis showed that overall an additive effect of the combinations was obtained. Ketorolac and sunitinib inhibited colony formation of RXF A-498 cells seeded in soft agar in a concentration-dependent manner. This is also reflected in the matrix combination, where activity of the different combinations was observed with increasing test concentrations of both compounds. Bliss independence analysis showed that the combination of ketorolac and sunitinib was synergistic at mid concentration levels of ketorolac (125 μM to 500 μM) and sunitinib (0.625 μM to 2.5 μM). As shown in FIGS. 3 and 4, is a consistent effect pointing towards synergy (BI>0.15).

Example 5

In vivo Animal Efficacy Study

10 Healthy female athymic nude mice were recruited for the donor cell inoculation. Animals were subcutaneously injected at flank region with 10 million A498 cells suspended in 200 μl of media and matrigel. Animals were monitored for solid tumor growth. Once the tumor reaches ~500 mm³, donor animals were humanely sacrificed and tumors were collected under aseptic condition. Tumors were fragmented in to ~30 mg size.

After one week of acclimatization, female athymic nude mice were subcutaneously implanted with ~30 mg tumor fragments. Animals were observed for tumor growth for the following three weeks. The tumor bearing animals were selected from the experimental animals and grouped on basis of tumor size, into six groups containing 7 animals in each group:

Group (G1) animals served as a vehicle control, which received 10 mL/kg, p.o. of 0.5% CMC in water;

Group 2 (G2) served as the standard, which received 20 mg/kg (sub-therapeutic dose) of sunitinib;

Group 3 (G3) received ketorolac at 5 mg/kg;

Group 4 (G4) received ketorolac at 10 mg/kg+sunitinib at 20 mg/kg;

Group 5 (G5) received ketorolac at 5 mg/kg+sunitinib at 20 mg/kg;

Group 6 (G6) received ketorolac at 10 mg/kg+sunitinib at 20 mg/kg.

| Group | Treatment | Dose, Route & Regimen | No. of Animals |
|---|---|---|---|
| G1 | Vehicle, 0.5% CMC | 10 mL/kg, p.o. q.d. × 21 | 7 |
| G2 | Sunitinib | 20 mg/kg, p.o. q.d. × 21 | 7 |
| G3 | Ketorolac | 5 mg/kg, p.o. q.d. × 21 | 7 |
| G4 | Ketorolac | 10 mg/kg, p.o. q.d. × 21 | 7 |
| G5 | Ketorolac + Sunitinib | 5 mg/kg, p.o. q.d. × 21 + 20 mg/kg, p.o. q.d. × 21 | 7 |
| G6 | Ketorolac + Sunitinib | 10 mg/kg, p.o. q.d. × 21 + 20 mg/kg, p.o. q.d. × 21 | 7 |

Tumor Measurement

The tumor sizes were measured weekly twice from the date of tumor appearance till the end of the experiment. Tumor size was measured by digital vernier caliper (MITUTOYO) by measuring length (L=longest axis) and width (W=shortest axis). Tumor Volume was calculated using the formula: $L \times W^2/2$ (Unit: mm³), wherein L=Length of tumor (mm) and W=Width of tumor (mm). Form the tumor volume data mean tumor volume and % tumor growth inhibition (% TGI) were calculated (SEM=standard error of mean).

Figure 5:
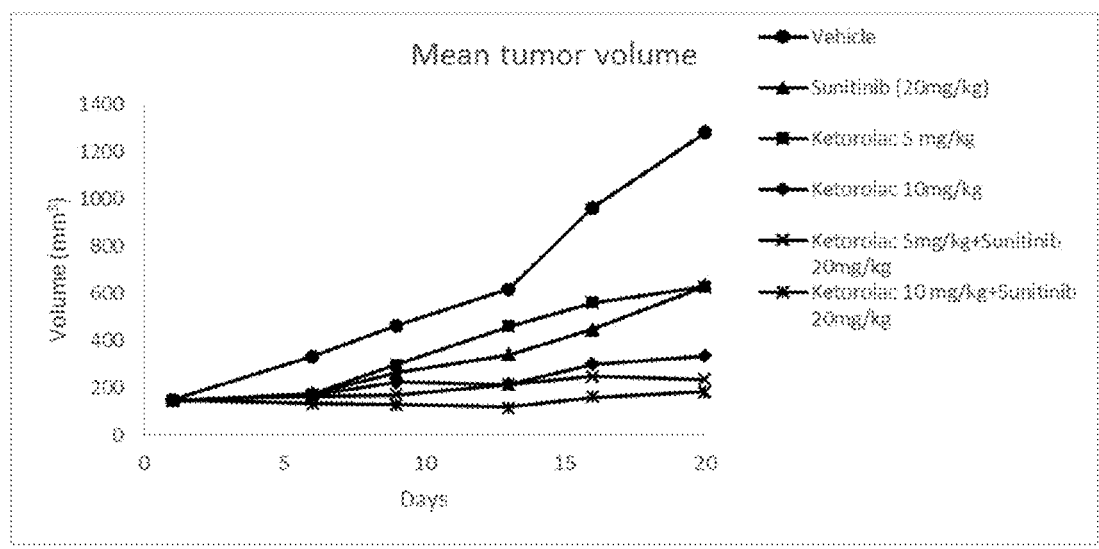
FIG. 5 depicts tumor volume growth in mice treated with ketorolac, alone or in combination with sunitinib.

Mean Tumor Volume (FIG. 5)

| Day | G1 Mean SEM | G2 Mean SEM | G3 Mean SEM | G4 Mean SEM | G5 Mean SEM | G6 Mean SEM |
|---|---|---|---|---|---|---|
| 1 | 147.56 | 145.40 | 145.65 | 145.79 | 148.71 | 146.91 |
|   | 20.68 | 29.19 | 24.66 | 23.78 | 31.09 | 30.78 |
| 6 | 331.93 | 174.90 | 174.13 | 168.10 | 164.60 | 133.31 |
|   | 79.52 | 37.07 | 35.50 | 23.48 | 39.20 | 26.27 |
| 9 | 463.77 | 261.95 | 297.42 | 223.78 | 170.27 | 126.99 |
|   | 110.07 | 66.94 | 87.10 | 41.15 | 72.68 | 51.68 |
| 13 | 617.07 | 340.62 | 460.01 | 215.58 | 213.84 | 118.23 |
|   | 146.04 | 93.64 | 216.57 | 43.13 | 109.53 | 54.24 |
| 16 | 961.26 | 448.05 | 559.69 | 300.44 | 247.04 | 161.38 |
|   | 226.49 | 121.72 | 209.10 | 69.77 | 150.63 | 61.71 |
| 20 | 1280.51 | 630.25 | 626.62 | 336.27 | 235.40 | 183.22 |
|   | 295.87 | 215.72 | 240.41 | 99.18 | 150.77 | 80.92 |

Figure 6:
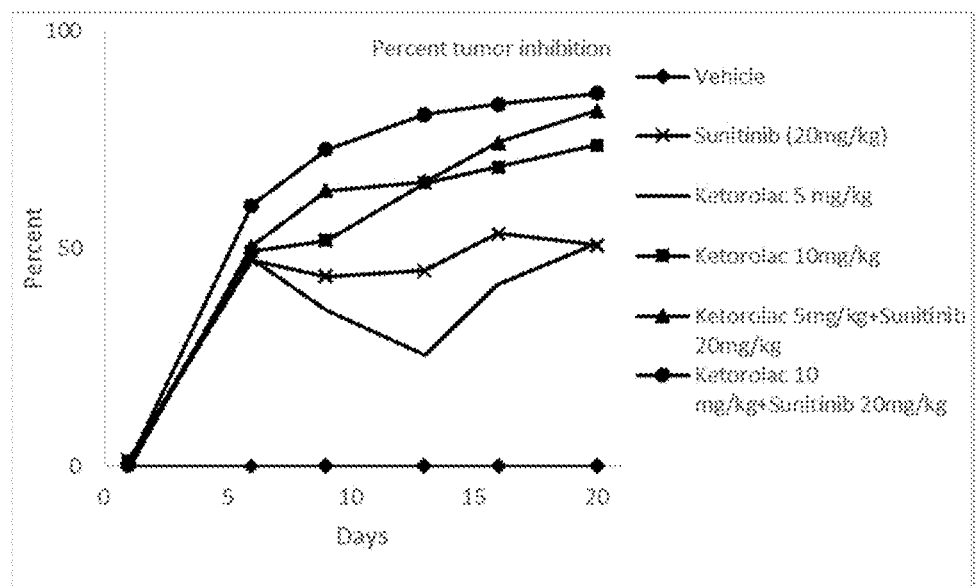
FIG. 6 depicts tumor growth inhibition in mice treated with ketorolac, alone or in combination with sunitinib.

Tumor Growth Inhibition (FIG. 6)

| Days | G1 | G2 | G3 | G4 | G5 | G6 |
|---|---|---|---|---|---|---|
| 1 | 0 | 1.47% | 1.29% | 1.20% | −0.78% | 0.44% |
| 6 | 0 | 47.31% | 47.54% | 49.36% | 50.41% | 59.84% |
| 9 | 0 | 43.52% | 35.87% | 51.75% | 63.28% | 72.62% |
| 13 | 0 | 44.80% | 25.45% | 65.06% | 65.35% | 80.84% |
| 16 | 0 | 53.39% | 41.77% | 68.75% | 74.30% | 83.21% |
| 20 | 0 | 50.78% | 51.06% | 73.74% | 81.62% | 85.69% |

Figure 7:
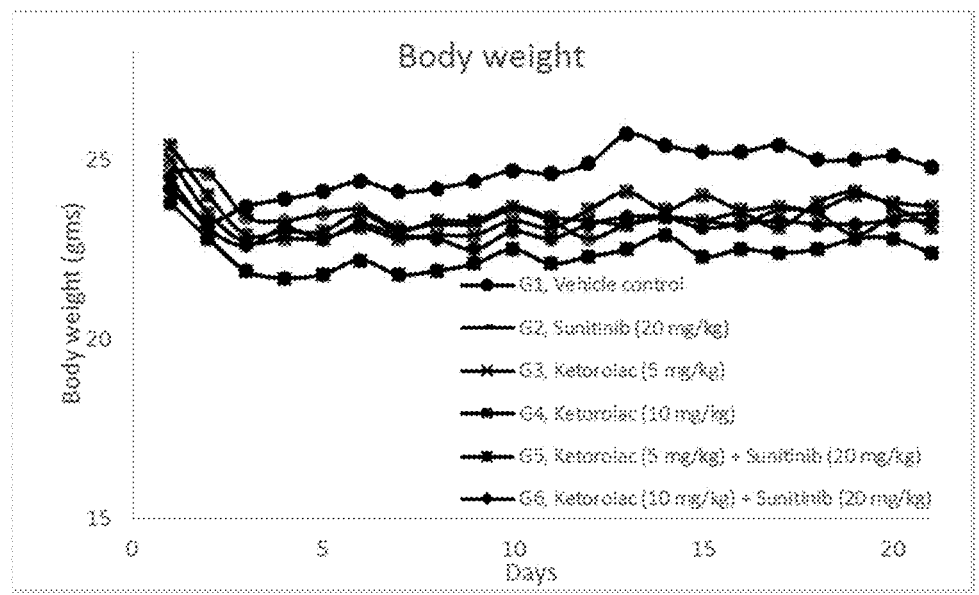
FIG. 7 depicts body weight change in mice treated with ketorolac, alone or in combination with sunitinib.

Body weight changes for each group are reported in FIG. 7. From the data, it is evident that ketorolac by itself shows anti-tumor efficacy. It inhibits tumor formation by up to 51% and 73% on day 20 when used at 5 mg/kg and 10 mg/kg respectively. Sunitinib alone at a dose of 20 mg/kg show a maximum tumor inhibition of 51%. In combination with Sunitinib, 81% and 85% tumor inhibition was obtained when used with 5 mg/kg and 10 mg/kg ketorolac respectively. Ketorolac in combination with Sunitinb shows more than additive effect in inhibiting tumor growth, moreover no antagonistic effect was seen in any of the combination at any stage of the experiment. Furthermore, none of the treatment groups shows any significant change in body weights Example 6

PAR-4 Activity

Figure 8:
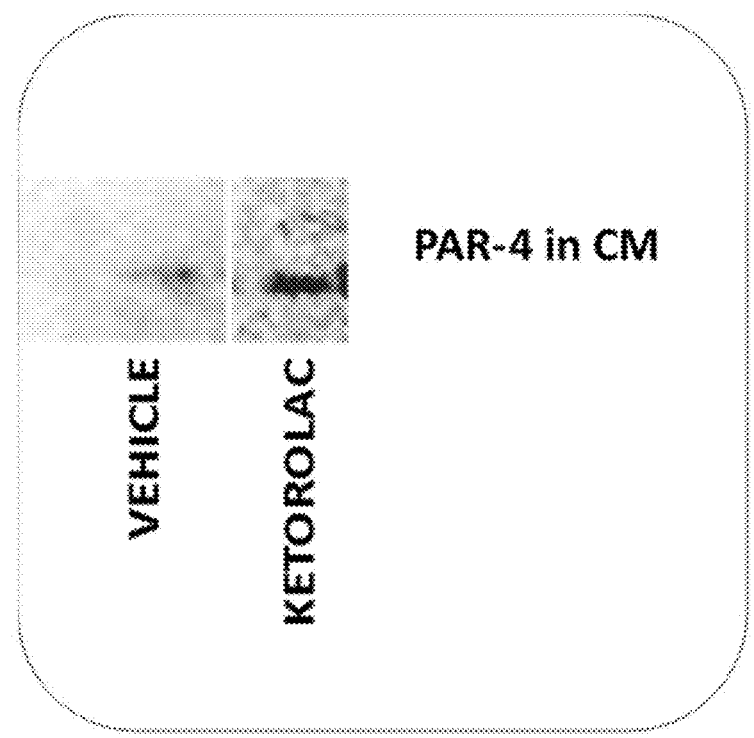
FIG. 8 depicts induction of PAR-4 by ketorolac from mouse embryonic fibroblast cells.

Mouse embryonic fibroblast cells were harvested from exponential phase cultures. After a 24 h recovery period to allow the cells to resume exponential growth the cells were treated with 25 µM of ketorolac followed by further 18-21 h of incubation. Induction of Par-4 was checked in the cell supernatant and cell lysate by subjecting the samples to Western blot analysis with antibodies specific for Par-4. The samples were also subjected to SDS/PAGE and Coomassie blue staining to determine albumin levels in serum from the CM as another loading control. As shown in FIG. 8, ketorolac was able to induce robust Par-4 secretion in the cell supernatant from normal mouse embryonic fibroblast cells in a dose dependent manner.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for the treatment of renal cell carcinoma in a patient, the method comprising administering to said patient ketorolac, or a pharmaceutically acceptable salt or ester thereof, in an amount effective to treat renal cell carcinoma.

2. The method according to claim 1, wherein the renal cell carcinoma comprises treat conventional (clear-cell) renal cell carcinoma, papillary renal cell-carcinoma, chromophobe renal carcinoma, onco-cytoma, or collecting-duct carcinoma.

3. The method according to claim 1, wherein the renal cell carcinoma comprises Stage I, Stage II, Stage III or Stage IV renal cell carcinoma.

4. The method according to claim 1, wherein ketorolac is administered in combination with at least one other cancer therapy.

5. The method according to claim 4, wherein the additional cancer therapy comprises surgery, chemotherapy, immunotherapy, or ionizing radiation.

6. The method according to claim 5, wherein the additional cancer therapy comprises administering at least one additional chemotherapeutic agent comprising a nucleoside analogue, antifolate, antimetabolite, topoisomerase I inhibitor, anthracycline, podophyllotoxin, taxanes, vinca alkaloid, alkylating agent, platinum compound, proteasome inhibitor, nitrogen mustard, oestrogen analogue, monoclonal antibody, tyrosine kinase inhibitor, mTOR inhibitor, retinoid, immunomodulatory agent, histone deacetylase inhibitor, or other kinase inhibitor.

7. The method according to claim 6, wherein the additional chemotherapeutic agent comprising a tyrosine kinase inhibitor.

8. The method according to claim 7, wherein the additional chemotherapeutic agent comprises sunitinib, or a pharmaceutically acceptable salt thereof.

9. The method according to claim 4, wherein the additional cancer therapy comprises treatment with ionizing radiation.

10. The method according to claim 4, wherein the additional cancer therapy comprises surgical treatment for renal cell carcinoma.

11. A method for treating cancer, comprising administering ketorolac, a pharmaceutically acceptable salt or ester thereof, to a patient in need thereof, in an amount effective to increase expression of prostate apoptosis response 4 (PAR-4).

12. The method according to claim 11 wherein the method further comprises administering at least one additional cancer therapy.

13. The method according to claim 12, wherein the additional cancer therapy comprises administering one or more additional chemotherapeutic agents.

14. The method according to claim 12, wherein the additional cancer therapy comprises administering ionizing radiation to the patient.

15. The method according to claim 12, wherein the additional cancer therapy comprises a surgical intervention.

* * * * *